(12) United States Patent
Nord et al.

(10) Patent No.: US 7,796,731 B2
(45) Date of Patent: Sep. 14, 2010

(54) LEAF SEQUENCING ALGORITHM FOR MOVING TARGETS

(75) Inventors: Janne Ilmari Nord, Espoo (FI); Sami Pekka Siljamaki, Espoo (FI); Tuomas Erik Torsti, Espoo (FI)

(73) Assignee: Varian Medical Systems International AG, Zug (CH)

( * ) Notice: Subject to any disclaimer, the term of this patent is extended or adjusted under 35 U.S.C. 154(b) by 0 days.

(21) Appl. No.: 12/196,639

(22) Filed: Aug. 22, 2008

(65) Prior Publication Data

US 2010/0046713 A1   Feb. 25, 2010

(51) Int. Cl.
*A61N 5/10* (2006.01)
*G21K 5/10* (2006.01)
*G21K 1/02* (2006.01)

(52) U.S. Cl. ............................ 378/65; 378/69; 378/149

(58) Field of Classification Search .................... 378/64, 378/65, 69, 145, 147–152, 204, 205; 600/427–429; 606/130; 250/363.1, 503.1, 505.1
See application file for complete search history.

(56) References Cited

U.S. PATENT DOCUMENTS

| | | | | |
|---|---|---|---|---|
| 6,144,875 A | * | 11/2000 | Schweikard et al. | 600/427 |
| 6,307,914 B1 | * | 10/2001 | Kunieda et al. | 378/65 |
| 6,757,355 B1 | * | 6/2004 | Siochi | 378/65 |
| 6,907,105 B2 | * | 6/2005 | Otto | 378/65 |
| 7,020,245 B2 | * | 3/2006 | Noguchi | 378/150 |
| 7,221,733 B1 | * | 5/2007 | Takai et al. | 378/65 |
| 7,507,975 B2 | * | 3/2009 | Mohr | 250/492.1 |
| 7,551,717 B2 | * | 6/2009 | Tome et al. | 378/65 |
| 2007/0076846 A1 | * | 4/2007 | Ruchala et al. | 378/65 |
| 2007/0201613 A1 | * | 8/2007 | Lu et al. | 378/65 |
| 2008/0144772 A1 | * | 6/2008 | Yi et al. | 378/65 |
| 2008/0159478 A1 | * | 7/2008 | Keall et al. | 378/65 |
| 2008/0298550 A1 | * | 12/2008 | Otto | 378/65 |

OTHER PUBLICATIONS

Murphy, Martin J., Tracking Moving Organs in Real Time, Jan. 2004, Seminars in Radiation Oncology, Stanford University, vol. 14, No. 1, pp. 91-100.*

* cited by examiner

*Primary Examiner*—Edward J Glick
*Assistant Examiner*—Anastasia Midkiff
(74) *Attorney, Agent, or Firm*—Townsend and Townsend and Crew LLP

(57) ABSTRACT

A method of providing intensity modulated radiation therapy to a moving target is disclosed. The target moves periodically along a trajectory that is projected onto a multi-leaf collimator (MLC) plane. The MLC plane is divided into thin slices parallel to the movement of the target. The present invention optimizes the leaf sequence such that, within each slice, if a point receives radiation, all other points in that slice that receive the same amount or more fluence are also receiving radiation at the same time.

20 Claims, 5 Drawing Sheets

LEAF SEQUENCING ALGORITHM FOR MOVING TARGETS

FIELD OF THE INVENTION

The present invention is related to radiation therapy systems using multi-leaf collimators, and is particularly related to a leaf sequencing algorithm for treating moving targets and a method of implementing such an algorithm.

BACKGROUND OF THE INVENTION

Radiation therapy for cancer treatment has been in use for several decades. Modern radiation therapy systems typically generate high intensity x-rays by bombarding a suitable target with high energy electrons. X-rays are emitted from the target in a generally conical pattern and are initially confined to a generally rectangular beam by moveable, x-ray blocking "jaws" in the head of the system. Typically, the patient is positioned about 1 meter from the x-ray target and, when fully open, the jaws define a square treatment area that is about 40 cm×40 cm at the patient plane. However, in many instances it is important to irradiate only a precisely defined volume conforming to a tumor, thus the target site must be irradiated from multiple angles. Rarely, however, can the system jaws alone be used to implement a suitable treatment plan. While the use of x-rays is the predominant technique for radiation therapy, high energy particles, such as electrons and protons, are also sometimes used. Accordingly, as used herein the term radiation therapy is intended to encompass all such techniques, and the present invention has application to all such techniques. Thus, when reference is made herein to x-rays or radiation, such terms should be also understood to encompass high energy particles.

Multi-leaf collimators (MLCs), such as described in the co-assigned U.S. Pat. No. 4,868,843, issued Sep. 19, 1989, to Nunan, (the disclosure of which is incorporated by reference), have been almost universally adopted to facilitate shaping of the radiation beam so that the beam conforms to the site being treated, i.e., the leaves are adjusted so that the beam conforms to the shape of the tumor from the angle of irradiation. Subsequent to its introduction, the MLC has also been used to perform a technique known as "Intensity Modulated Radiotherapy" (IMRT), which allows control over the radiation doses delivered to specific portions of the site being treated. In particular, IMRT allows the intensity distribution of the radiation reaching the patient to have almost any arbitrary distribution. IMRT can be implemented by iteratively positioning the leaves of the MLC, which form an aperture through which radiation is delivered, to provide desired field shapes which collectively deliver the desired dose distribution. IMRT techniques can either be static ("point and shoot"), in the sense that the leaves do not move when the beam is on or, alternatively, as in systems sold by the assignee of the present invention, be implemented using a "sliding window" approach, in which the leaves of the MLC are moved continuously when the beam is on. IMRT is typically implemented by using an elongated aperture or window that is oriented perpendicular to the direction of leaf motion, as depicted in FIG. 5. Specifically, in sliding window IMRT the overall speed of leaf motion and the separation of leaf pairs are independently adjusted as the window moves, such that different portions of the treatment field are irradiated with different doses of radiation through an aperture that changes shape as it is being moved.

Radiation therapy is generally implemented in accordance with a treatment plan which typically takes into account the desired dose of radiation that is prescribed to be delivered to the tumor, as well as the maximum dose of radiation which can be delivered to surrounding tissue. Various techniques for developing treatment plans are well known. Preferably, the computer system used to develop the treatment plan provides an output that can be used to control the radiation therapy system, including the MLC leaf movements. Typically, the desired dose prescribed in a treatment plan is delivered over several sessions, called fractions.

Tumors and surrounding tissue, including critical organs, may move in a periodic fashion while a site is being irradiated, for example, as a result of normal respiratory motion. (As used herein "periodic" is meant to have a broad meaning and includes any repeated motion, such as breathing motion, even if irregular.) Heretofore, no effort has been made to take such movement into account when developing a treatment plan and, therefore, movement in the treatment field can have a significant impact on the effectiveness of a treatment plan. A treatment plan that does not take such movement into account may result too much or too little radiation reaching the intended target region and/or too much radiation reaches surrounding tissue. The extent of the problem caused by the mismatch varies, and can range, in extreme cases, from very little radiation delivered to the target to a delivery of several times the intended dose. Other types of deviations from the prescribed radiation delivery may occur, causing additional problems with the effectiveness of the treatment plan.

The quantity of incident radiation, or fluence, delivered is a sum of the radiation allowed through the aperture over the course of the exposure. In the worst case scenario, the target region may receive several times the prescribed dose when the target region movement is in phase with the aperture movement. On the other hand, if movement of the target region is out of phase with the window movement, the tumor may receive a lower than prescribed dose, or no dose. In practice, interplay between these movements has been reported to generate differences of greater than 10% between the delivered and the planned dose distributions for a single fraction. Obtaining the desired biological response in the target region depends upon delivery of the intended fractional dose, thus achieving the planned dose distribution is critical to success of the treatment.

SUMMARY OF THE INVENTION

The present invention provides a method of performing intensity modulated radiotherapy (IMRT) for a moving target that reduces the undesirable effects between the beam from a multi-leaf collimator (MLC) and a target region that moves periodically along a path or trajectory.

The inventors have determined that the extent of the moving target problem depends largely on how the target region and the radiation beam delivered through the MLC move in relation to each other. Because the features of the radiation beam (e.g., shape, position, movement) are determined by the leaf sequence, the inventors have further determined that the extent of adverse effects due to mismatch depend on the relationship between the movement of the target region and of the leaves. The target region and the leaves may move at similar or dissimilar speeds and may, or may not be, in phase.

According to a preferred method of the present invention, the trajectory of target motion is, preferably, oriented to be perpendicular to the leaves of the MLC, such that movement of the leaves, and the aperture created by the MLC leaves, is perpendicular to the trajectory of the moving target. The aperture in the MLC through which radiation passes is typically elongate in a direction that is parallel to the target trajectory. The method of the invention produces a much narrower range of variation from the prescribed dose for a given area, which is a significant improvement over prior art models where the dose can be much higher or lower than the intended maximum dose, as discussed above. As a result, the moving target receives a fluence that is closest to the desired fluence.

In summary, the present invention is directed to the generation and use of leaf sequences in a treatment plan where, within each slice on the MLC plane, if a point receives radiation, then all other points irradiated through the same slice that are supposed to receive the same amount or more fluence receive radiation at the same time as that point. Essentially, this approach allows the radiation dose to be built up within each slice such that higher doses of radiation are delivered to gradually smaller regions of the slice, until the maximum for the slice is reached.

DETAILED DESCRIPTION

Radiation therapy begins with the development of a treatment plan for delivering a prescribed dose of radiation to a tumor while minimizing the dose of radiation delivered to surrounding tissue. The treatment plan prescribes the amount of fluence each portion of target region should receive, but there are many leaf sequences (i.e., many combinations of leaf movements) that can be used to produce a given fluence. Moreover, treatment plans typically provide for irradiating the target from multiple angles. Heretofore, treatment planning has proceeded on the basis that the treatment volume is stationary while the patient is being irradiated, i.e., target motion was not taken into consideration. Thus, prior art treatment planning made no effort to optimize leaf movements in relation to target motion. As discussed above, the present invention is directed to the problem which arises when the treatment volume moves while being irradiated. In one aspect, the present invention addresses the problem by taking into account the interplay effects between leaf movements and target movements, as discussed herein.

Figure 1A:
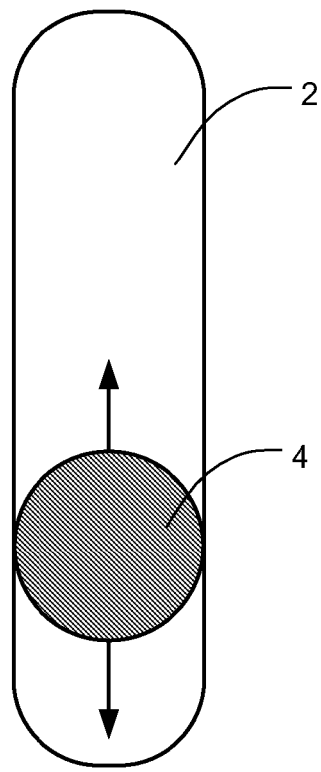
FIG. 1A is a representation of a moving target and the region through which the target moves.

As noted, the treatment volume may move in a periodic fashion along a trajectory. For purposes of the present invention the trajectory of motion is modeled as a single path, even if there is some variation in the actual motion. In most instances, the trajectory of any point in the treatment area can reasonably be approximated by a line segment, although the present invention is not limited to motion along linear trajectories. This trajectory can be projected onto the MLC plane, which is the plane is defined by the face of the MLC closest to the patient. This MLC plane is substantially orthogonal to the center of the radiation beam. FIG. 1A shows a "snapshot" of a portion of a treatment area 4 that moves (sometimes referred to herein as a moving target). Area 4 may be thought of as a tumor or portion of a tumor which is prescribed to receive a certain fractional dose of radiation. The area surrounding target 4 may be, for example, a different region of the tumor for which a different fractional dose is prescribed. Motion of the moving target 4 along a trajectory (as illustrated by the arrows) defines a larger region 2 through which the target moves in a periodic manner. Such motion may be caused, for example, by respiration. In FIG. 1A, the trajectory is a line segment. In many instances, even if the moving target does not follow a linear trajectory, it is possible to obtain the benefits of the present invention by approximating the trajectory as a line. Use of a linear trajectory is simple and convenient, and provides most of the advantages of the present invention when applied to actual treatment cases. More generally the trajectory can be curved, as discussed in further detail below.

Figure 1B:
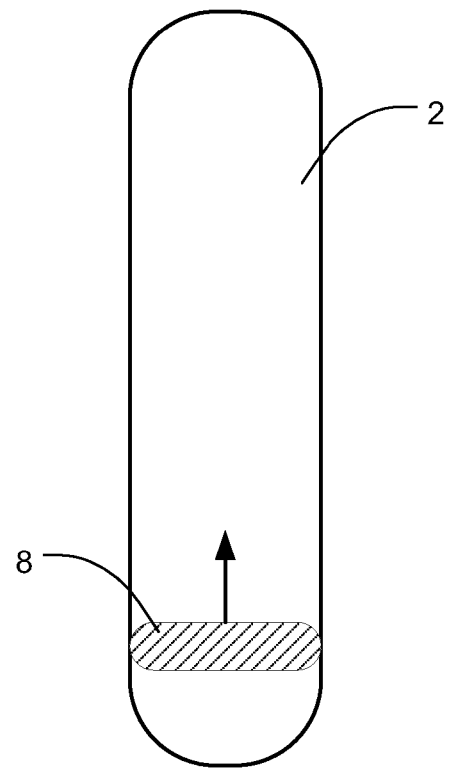
FIG. 1B is a representation of the radiation reaching the area of FIG. 1A through an MLC aperture that is not optimized to take into account target motion.

FIG. 1B is a "snapshot" representation of the radiation beam 8 projected onto a portion of region 2 through an aperture in an MLC created by opposing leaf pairs. In an unoptimized treatment plan radiation beam 8 may move in a direction that is parallel to the trajectory of the moving target (as indicated by the arrow). In other words, the MLC aperture is orthogonal to the trajectory of target motion. The movement of radiation beam 8 can be in connection with either a sliding window IMRT technique or a point and shoot technique.

Figure 2A:
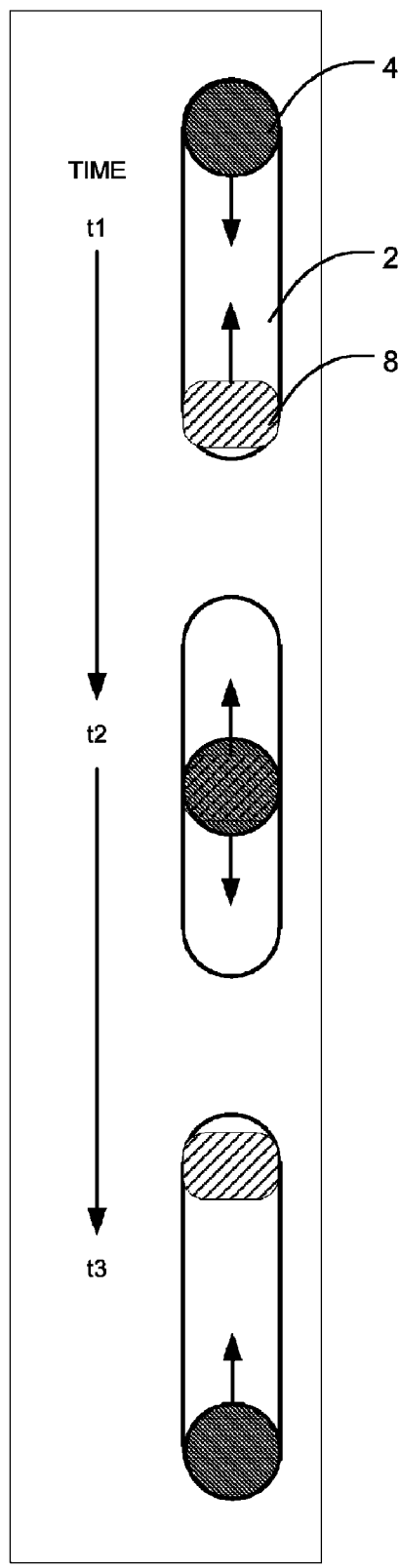
FIGS. 2A and 2B show time lapse representations of the un-optimized sliding window IMRT with apertures parallel to target movement.
Figure 2B:
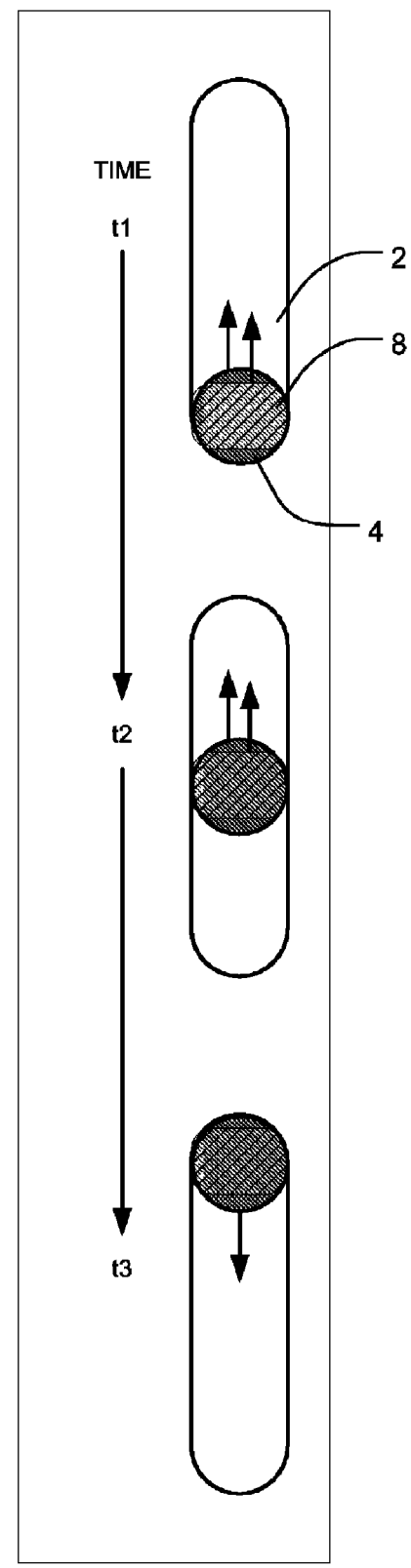

FIGS. 2A and 2B illustrate in further detail the interplay effects in an un-optimized sliding window IMRT system. Both figures show a target 4 moving within region 2 along a trajectory, where the sliding window aperture, and hence radiation beam 8, moves at approximately the same rate. In both cases, direction of movement of beam 8 is generally parallel to the direction of movement of the target 4 and in both figures beam 8 moves from bottom to top. FIG. 2A, shows three positions of target 4 and the radiation beam 8 as they move through area 2, indicated by time markers t1, t2 and t3. In FIG. 2A, since the target 4 moves from top to bottom, while the beam 8 moves from bottom to top at approximately the same speed, the movement results in the target 4 and the beam 8 intersecting generally in the center of region 2, as shown at time marker t2. In this case, movement of the aperture thus provides a dose to target 4 that is approximately equal to the prescribed dose.

In contrast, FIG. 2B shows three positions of the target 4 as both it and beam 8 move from bottom to top at the same speed. Thus, the motions of target 4 and beam 8 are "in phase" with one another. In comparison to FIG. 2A, the movement shown in FIG. 2B results in the continued overlap of beam 8 with target 4 throughout the entire time radiation is delivered to area 2. This provides a dose that is much greater than the prescribed dose. Indeed, in the situation depicted in FIG. 2B, the dose is several times the prescribed dose. FIGS. 2A and 2B exaggerate the interplay effect due to the fact that the target and beam move at substantially the same speed. Moreover, this makes the phase, i.e., the starting position of the target relative to the beam, critical. Nonetheless, those skilled in the art will understand that the problem of interplay effects due to target motion will cause unoptimized results in many other circumstances.

Figure 3:
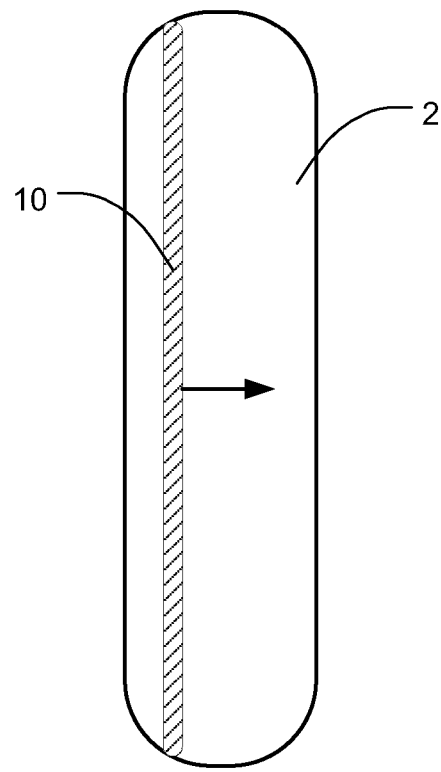
FIG. 3 is a representation of radiation reaching the area of FIG. 1A through an MLC aperture according to an embodiment of the present invention.

Unlike the unoptimized MLC orientation of FIGS. 1B, 2A and 2B, the present invention orients the MLC to use apertures that are generally parallel to the trajectory of the target movement. One consequence of this orientation is that the apertures are generally longer in the direction of target movement, and preferably extend substantially the length of area 2. According to an embodiment of the present invention, FIG. 3 shows a radiation beam 10 reaching area 2 through an MLC aperture that extends parallel with and moves perpendicularly to the trajectory that defines region 2. (Region 2 in FIG. 3 is the same as in FIGS. 1A, 1B, 2A and 2B.)

Figure 4A:
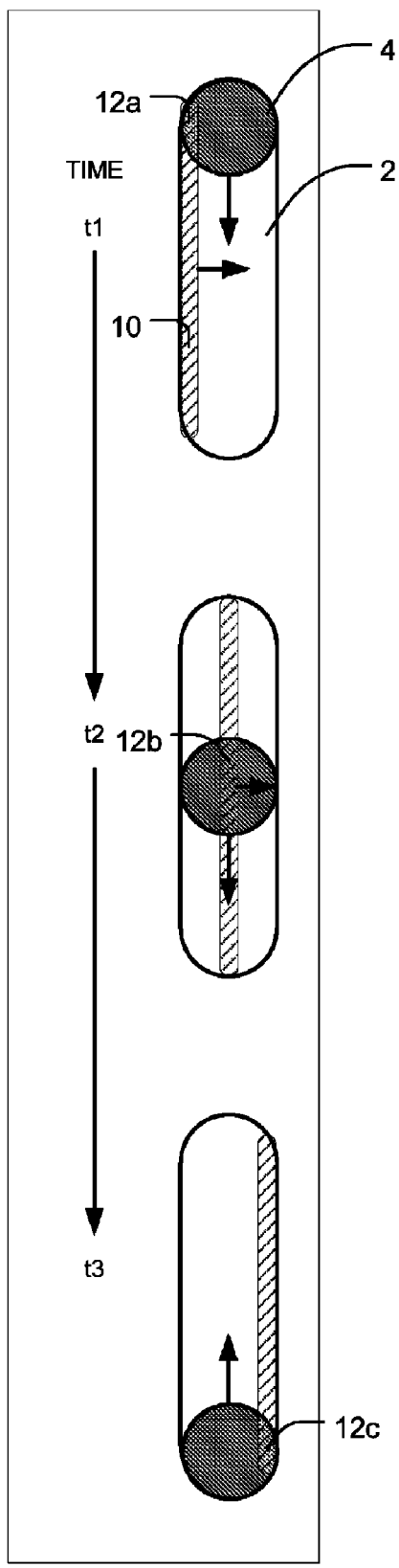
FIGS. 4A and 4B show time lapse representations of sliding window IMRT according to an embodiment of the present invention.
Figure 4B:
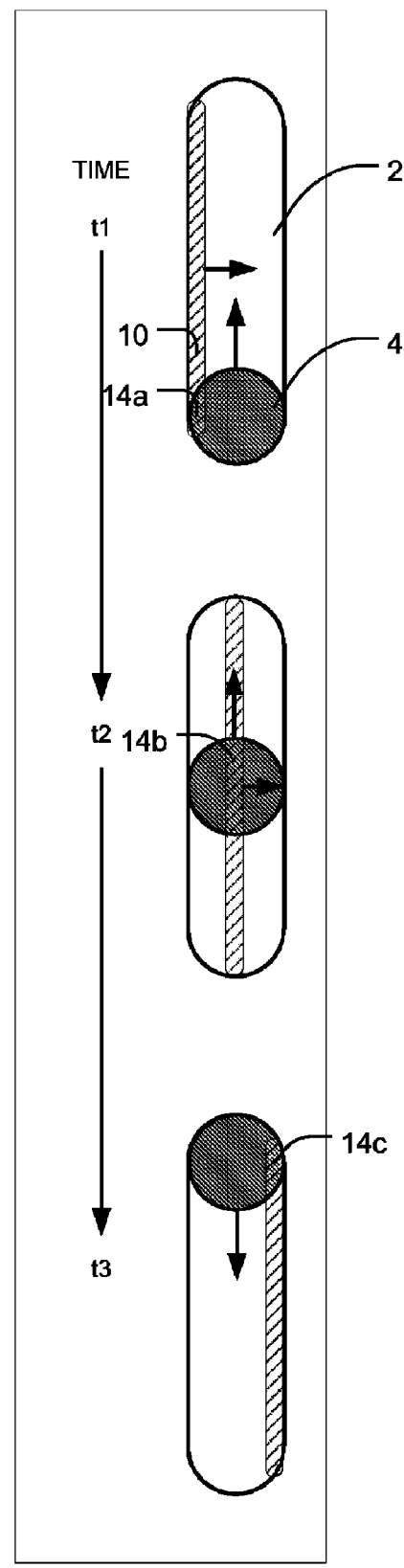

FIGS. 4A and 4B are similar to FIGS. 2A and 2B, showing the same target 4 movement at times t1, t2 and t3; however, they illustrate an optimized sliding window IMRT according to an embodiment of the present invention, wherein the beam motion and target motion are orthogonal. In FIG. 4A, as target 4 moves from top to bottom in region 2, beam 10 moves across the region from left to right from time t1 to t3. Thus, the movement of the beam (and hence the MLC slice or aperture) is orthogonal to the target trajectory. As a result, at all times throughout the delivery period at least some portion (e.g., 12a, 12b, 12c) of the target 4 is receiving radiation. Similarly, as shown in FIG. 4B, when the target 4 moves from bottom to top, sections 14a, 14b, 14c receive radiation as aperture 10 moves across region 2. Thus, regardless of the phase relationship between the target and the beam, i.e., where target 4 is at the beginning of the radiation delivery, beam 10 will deliver approximately the prescribed dose to the target. Moreover, the dose delivered to the entire region 2 is the same in both cases.

Figure 5:
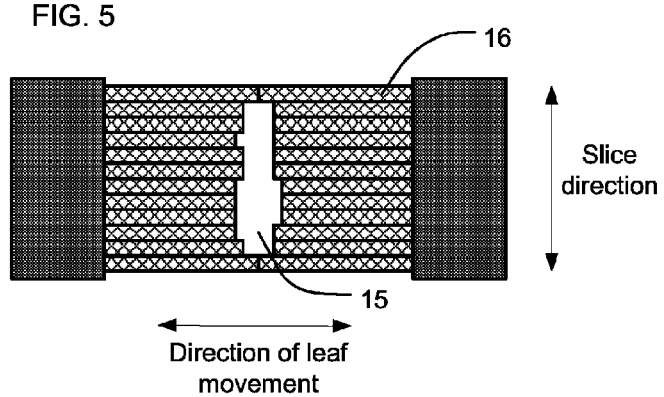
FIG. 5 is a representation of an MLC showing the leaves forming an aperture.

FIG. 5 shows an exemplary MLC plane having a plurality of leaves 16, arranged in opposing pairs, and an aperture 15 created by selected leaf movements, in well known fashion. Radiation passes through and is shaped by aperture 15 to create beam 10. In IMRT, aperture 15 is moved continuously (sliding window) or periodically (point and shoot) across the face of the MLC in either of the directions indicated in FIG. 5. As the aperture is moved its shape may be adjusted to control the fluence to different portions of the treatment volume, i.e., the combined leaf movements may be used, in known fashion, to vary the fluence delivered to the treatment area. An embodiment of the present invention uses leaf sequences wherein the beam through the MLC aperture is generally parallel to the motion of target 4 and substantially equal to the length of region 2. As beam 10 moves, the configuration of aperture 15, may be adjusted, thereby allowing additional control over the fluence delivered to the treatment area.

Figure 6A:
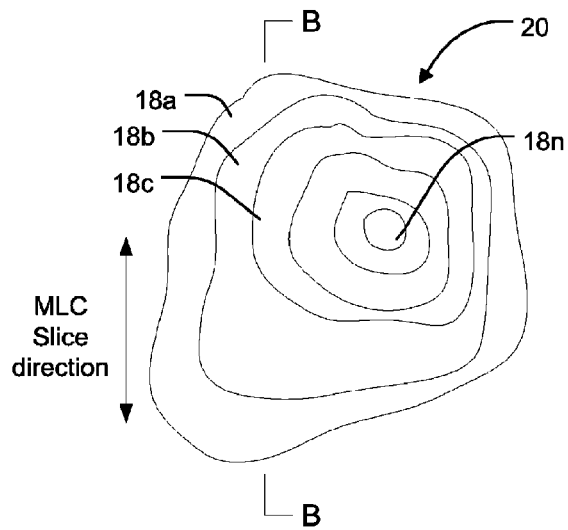
FIGS. 6A and 6B are a topographical visualization of a hypothetical fluence map delivered to a target region (6A) and along one slice in that region (6B).
Figure 6B:
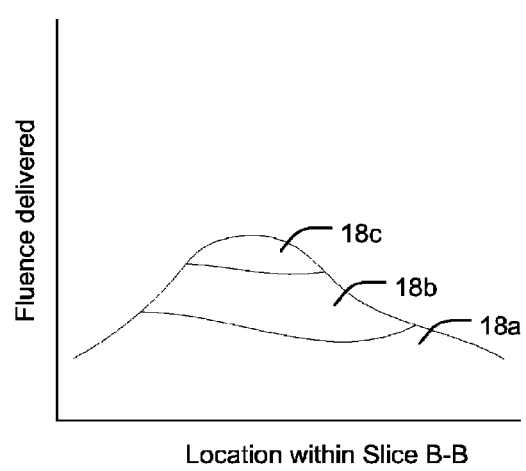

FIG. 6A depicts the fluence delivered to a treatment field in the form of a topographical fluence map 20, in accordance with an illustrative embodiment of the present invention. The lowest fluence represented in the map is in the generally annular region 18a, and the fluence increases to a maximum fluence region 18n. FIG. 6B shows the fluence received in the portion of the treatment area through the slice B-B of FIG. 6A. Slice B-B is aligned with the trajectory of movement. All of the points along slice B-B will receive a fluence that is between the lowest fluence 18a and a middle fluence 18c. Using the method of the present invention, the slices are aligned with the trajectory of the target's motion, thus even if a point in slice B-B were moving, it would not receive a higher fluence than the maximum for its slice, the middle fluence 18c. Accordingly, the present technique has limited the range over which the delivered dose may vary.

The MLC leaf movements of the present invention can be achieved with an algorithm similar to the one described in the co-assigned application entitled "Leaf Sequencing Algorithm To Reduce Tongue And Groove Effects" (U.S. patent application Ser. No. 12/267,044, now U.S. Pat. No. 7,609,811), the disclosure of which is incorporated by reference. According to the current invention, the leaf sequence is optimized to produce the field of radiation delivery for a moving target that more closely matches the intended dose. To form MLC slices parallel to the target region's movement, the leaves may most easily be oriented to move perpendicularly to that movement, but other orientations are possible. The leaf motion need not be oriented in the same direction as the movement of the aperture, although such orientation may simplify planning. However, there may be competing treatment considerations that make it necessary or desirable orient the MLC such that the angle of leaf movement is not orthogonal to the trajectory. According to an aspect of the present invention, the angle between the elongate apertures formed in the MLC and the trajectory is minimized.

The leaf movement may be perpendicular to the tumor movement (as shown in FIG. 5), allowing the leaves to modulate the fluence in all positions in one slice relatively quickly. Ideally, the orientation of the leaves is chosen based on the longest direction of the target field, such that they move perpendicularly to that direction as has been described. However, deciding on the orientation of the leaves is also influenced by the shape of the apertures that need to be formed in view of the shape of the tumor undergoing treatment. This is because some shapes present greater difficulties and can only be formed by a limited number of leaf arrangements. In some cases there will have to be a trade-off between the ideal orientation for the optimized leaf sequence based on the target movement and the physical constraints on the system for the leaves to form an aperture in the shape that is required. In such cases, the dose should be built up using the largest aperture possible that provides the precision needed.

In another embodiment of the invention, the optimization is fine-tuned by controlling the time each movement slice is exposed to radiation through the aperture. For example, if each slice intersects with the open aperture for about the duration of one movement cycle, the dose distribution is closer to the planned average distribution. In a further embodiment, a variable dose rate could be used to better control the exposure time for groups of slices. While timing the dose in this way is effective in conjunction with the present invention, and timing or gating in general is useful in a variety of applications, timing alone is not sufficient to avoid the interplay effects in an un-optimized system. Due to the periodic nature of the target movement and the difficulties in determining the precise location of the target 4 within region 2 at any given time, it is not practical to attempt to avoid phase problems, such as the overlapping situation shown in FIG. 3B, by simply timing the dose.

In a further embodiment of the invention, and as mentioned above, the trajectory of the target region may be curved. When the trajectory is not a simple line segment, but is curved or has some other shape, additional considerations must be taken into account in order to determine the proper orientation for the aperture and the related optimized leaf sequence. The best technique for handling a curved trajectory will depend on the exact shape and other aspects of the system, such as the physical constraints on leaf movement. In some cases, it may be sufficiently accurate and most efficient to simply map the trajectory to a predominant direction—a major axis of the trajectory curve, for example. In other cases, a rigid translation can be used to reduce the trajectories to a single direction, again, such as a predominant direction. This approach might be particularly useful for multiple, non-linear trajectories. Where the trajectory is more complex, it can be obtained from deformable image registration, in which imaging is used to find a best fit. There, features of the target region are matched in order to align the trajectory with a template image. With other complex trajectories, a point-specific movement model might be used to identify the trajectory, such as the use of boundary conditions to model the target region. Once the trajectory has been obtained, if necessary, the trajectory can be mapped or translated into a predominant direction as discussed above.

Figure 7:
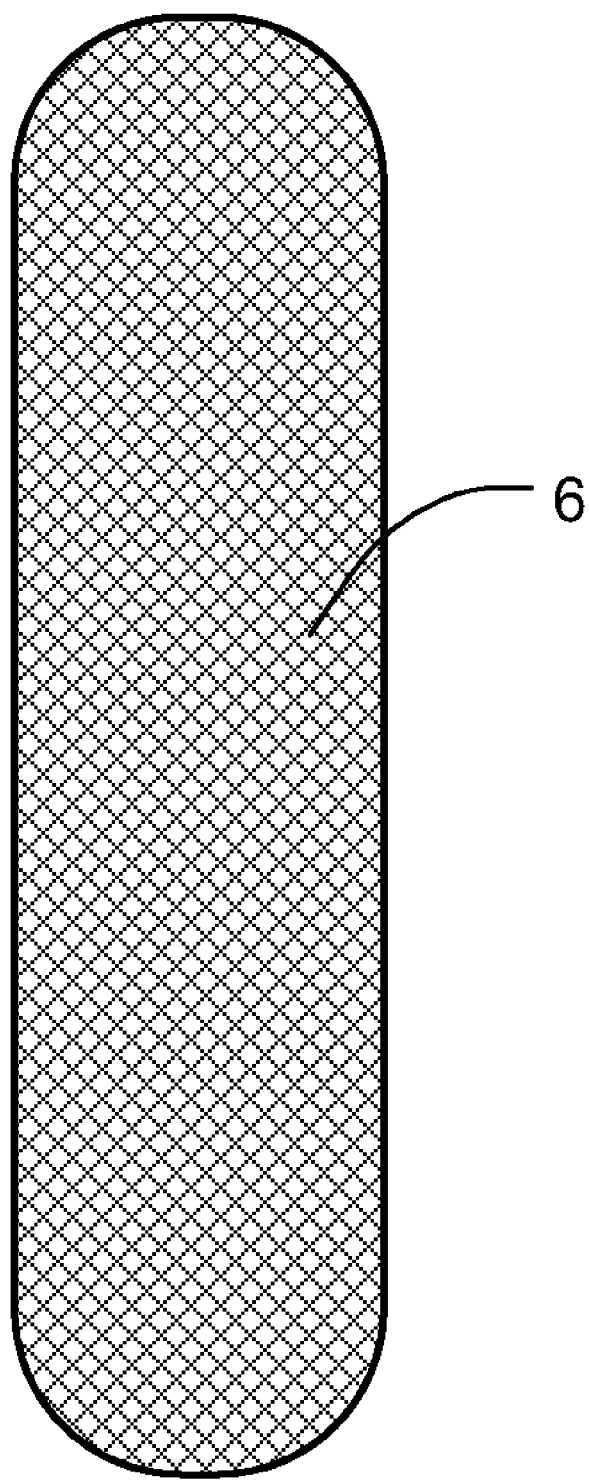
FIG. 7 is a representation of a target region having optimized fluence.

Ideally, as shown in FIG. 7, optimization of the sliding window IMRT system produces a fluence 6 that has the same value at all positions where it is possible for the tumor to be. Because target 4 only occupies a portion of region 2 at any one time, this ideal fluence may result in unnecessary irradiation of some portions of region 2. Specifically, in addition to target 4, region 2 may include healthy tissue which will be irradiated by the same dose as target 4. While this is not the most desirable situation, in many situations it is more important to ensure an adequate and even dose to the target 4 than to avoid irradiating the surrounding tissue. In this regard, it should be noted that this unnecessary irradiation of portions of region 2 also occurs using the un-optimized system. For example, in FIG. 3A the entire region 2 is irradiated, although target 4 only occupies a portion of the total area. Thus, except for when target 4 is exposed to the aperture 8 at time t2, the remainder of the radiation delivery to region 2 is unnecessary. Accordingly, the present invention provides an improved method for delivering radiation to a moving target, but further improvements to reduce the unnecessary radiation delivered to regions in the trajectory of the target would be beneficial.

The embodiments described above are illustrative of the present invention and are not intended to limit the scope of the invention to the particular embodiments described. Accordingly, while one or more embodiments of the invention have been illustrated and described, it will be appreciated that various changes can be made therein without departing from the spirit or essential characteristics thereof. Accordingly, the disclosures and descriptions herein are not intended to be limiting of the scope of the invention, which is set forth in the following claims.

What is claimed is:

1. A method of providing intensity modulated radiation therapy to a target using a multileaf collimator (MLC), wherein the target comprises a region that moves periodically along a trajectory, comprising:
   determining the trajectory of the moving target region;
   determining a line segment that at least approximately matches said trajectory;
   orienting the MLC such that all of the leaves of the MLC are perpendicular to said line segment;
   delivering therapeutic radiation through an aperture in said MLC, wherein each of said aperture and said target are in a first position; and
   delivering therapeutic radiation through an aperture in said MLC, wherein each of said aperture and said target are in a second position.

2. The method of claim 1, wherein the trajectory is linear and said line segment corresponds to said trajectory.

3. The method of claim 1, wherein the trajectory is a curve.

4. The method of claim 3, wherein the trajectory is obtained from deformable image registration or a point-specific movement model.

5. The method of claim 1, wherein said MLC aperture moves while said therapeutic radiation is delivered to the target.

6. The method of claim 5, wherein said MLC aperture is held in a fixed position each time said therapeutic radiation is delivered to the target.

7. An intensity modulated radiation therapy system for providing radiation therapy to a target, wherein the target comprises at least one region that moves periodically along a trajectory, comprising:
   a beam generator for creating a radiotherapy beam for irradiating the moving target region;
   a multi-leaf collimator positioned between said beam generator and said moving target region for controlling the shape and position of the beam;
   a control system having a computer-readable medium encoded with an algorithm including the steps of:
   projecting the trajectory of the moving target region onto a multi-leaf collimator plane; dividing the multi-leaf collimator plane into a plurality of thin slices substantially parallel to the movement of the target region; and
   generating a leaf sequence such that each point in a slice that receives the same fluence receives radiation at the same time.

8. The system of claim 7, wherein the trajectory is a line segment.

9. The system of claim 7, wherein the trajectory is a curve.

10. The system of claim 9, wherein the trajectory is obtained from deformable image registration or a point-specific movement model.

11. The system of claim 7, wherein generating the leaf sequence includes providing an aperture that is parallel to the movement of the target region.

12. The system of claim 11, further comprising controlling the time each slice is exposed to the aperture.

13. The system of claim 12, wherein each slice is exposed to the aperture for about the duration of one movement cycle.

14. The system of claim 13, further comprising providing a variable dose rate.

15. The system of claim 7, wherein the generated leaf sequence includes leaf movement that is perpendicular to the movement of the target region.

16. The system of claim 7, wherein the generated leaf sequence includes leaf movement that is not perpendicular to the movement of the target region.

17. A method of providing intensity modulated radiation therapy to a treatment volume using a multileaf collimator (MLC), wherein the treatment volume comprises a region that moves periodically along a trajectory, comprising:
   defining a line segment that corresponds to said trajectory;
   delivering radiation through a first elongate aperture in said MLC, when said aperture is in a first position; and
   delivering radiation through a second elongate aperture in said MLC, when said aperture is in a second position;
   wherein said first and second elongate apertures define first and second elongate axes that are offset from said line segment by first and second angles, and wherein said first and second elongate apertures are determined such that said first and second angles are minimized.

18. The method of claim 17 wherein said first and second elongate apertures are determined based on additional parameters.

19. The method of claim 17, wherein the trajectory is linear and said line segment corresponds to said trajectory.

20. The method of claim 17, wherein the trajectory is a curve.

* * * * *